(12) United States Patent  
Mullon

(10) Patent No.: US 12,109,344 B2
(45) Date of Patent: *Oct. 8, 2024

(54) IMPLANTABLE FLUID CONDUIT SYSTEM

(71) Applicant: Fresenius Medical Care Holdings, Inc., Waltham, MA (US)

(72) Inventor: Claudy J. Mullon, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 748 days.

This patent is subject to a terminal disclaimer.

(21) Appl. No.: 17/365,568

(22) Filed: Jul. 1, 2021

(65) Prior Publication Data

US 2021/0322659 A1 Oct. 21, 2021

Related U.S. Application Data

(63) Continuation of application No. 16/600,799, filed on Oct. 14, 2019, now Pat. No. 11,083,830.

(51) Int. Cl.
| | |
|---|---|
| *A61M 1/16* | (2006.01) |
| *A61M 1/34* | (2006.01) |
| *B29C 64/118* | (2017.01) |
| *B29C 64/321* | (2017.01) |
| B29K 67/00 | (2006.01) |

(52) U.S. Cl.
CPC ........ *A61M 1/1678* (2013.01); *A61M 1/1627* (2014.02); *A61M 1/34* (2013.01); *B29C 64/118* (2017.08); *B29C 64/321* (2017.08); *A61M 2205/3337* (2013.01); *A61M 2207/00* (2013.01);

(Continued)

(58) Field of Classification Search
CPC .... A61M 1/1678; A61M 1/1627; A61M 1/28; A61M 1/34; A61M 2205/3334; A61M 2205/3337; A61M 2207/00; A61M 2209/088; B29C 64/321
See application file for complete search history.

(56) References Cited

U.S. PATENT DOCUMENTS

| | | | |
|---|---|---|---|
| 8,241,239 B2 | 8/2012 | Solomon et al. | |
| 9,138,521 B2 * | 9/2015 | Solomon | B01D 63/026 |

(Continued)

FOREIGN PATENT DOCUMENTS

| | | |
|---|---|---|
| CN | 105579219 A | 5/2016 |
| WO | WO2021076235 | 8/2020 |

OTHER PUBLICATIONS

China National Intellectual Property Administration, "Chinese Application No. 202080086537.8, First Office Action dated Nov. 28, 2023, English and Chinese Translation" 23 pages.

(Continued)

*Primary Examiner* — Philip R Wiest
(74) *Attorney, Agent, or Firm* — Bass Patent Law, LLC

(57) ABSTRACT

A fluid conduit includes a first portion having a first porosity, a second portion disposed immediately adjacent to the first portion, the second portion having a second porosity that is greater than the first porosity, and a third portion of the fluid conduit disposed immediately adjacent to the second portion, the third portion having a third porosity that is less than the second porosity. Each of the first portion, the second portion, and the third portion may be integrally formed as a single, continuous piece defining the fluid conduit.

20 Claims, 6 Drawing Sheets

(52) U.S. Cl.
CPC .......... *A61M 2209/088* (2013.01); *B29K 2067/003* (2013.01)

(56) References Cited

U.S. PATENT DOCUMENTS

| | | | |
|---|---|---|---|
| 11,083,830 B2* | 8/2021 | Mullon | B29C 64/321 |
| 2003/0060695 A1 | 3/2003 | Connelly | |
| 2003/0060871 A1 | 3/2003 | Hill et al. | |
| 2004/0009096 A1 | 1/2004 | Wellman | |
| 2006/0058731 A1* | 3/2006 | Burnett | A61M 1/28 |
| | | | 604/29 |
| 2013/0122248 A1 | 5/2013 | Haselby et al. | |
| 2013/0178949 A1 | 7/2013 | Bowlin et al. | |
| 2014/0079758 A1 | 3/2014 | Hall et al. | |
| 2017/0165790 A1 | 6/2017 | McCarthy et al. | |
| 2017/0304858 A1 | 10/2017 | Leonard | |
| 2018/0353726 A1 | 12/2018 | Erbey et al. | |
| 2019/0054567 A1 | 2/2019 | Roerig et al. | |

OTHER PUBLICATIONS

Canadian Patent Office, "CA Application No. 3,156,116, Examiner's Report dated Dec. 18, 2023," 8 pages.
EPO, "EP Application No. 20877062.8, European Extended Search Report dated Sep. 19, 2023," 10 pages.
ISA/US, PCT Application No. PCT/US20/47931, International Search Report and Written Opinion mailed on Jan. 19, 2021, 12 pages.
U.S. Appl. No. 16/600,799, Notice of Allowance dated Apr. 14, 2021, 10 pages.

* cited by examiner

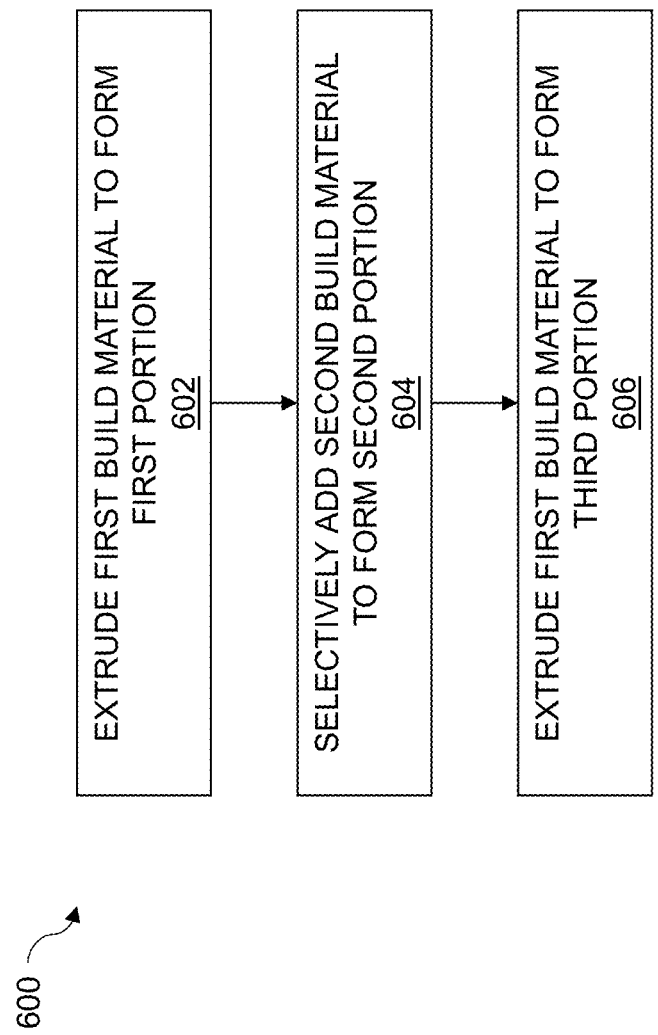

IMPLANTABLE FLUID CONDUIT SYSTEM

CROSS-REFERENCE TO RELATED APPLICATIONS

This application is a continuation of U.S. patent application Ser. No. 16/600,799 filed on Oct. 14, 2019, the entire content of which is hereby incorporated by reference in its entirety.

FIELD

The present disclosure generally relates to devices, systems, and methods for a fluid conduit, and more particularly, an implantable fluid conduit with an integral porous membrane.

BACKGROUND

Implantable fluid conduits may be used for a variety of applications, including without limitation selective removal or addition of components to or from the blood, such as the removal of water or toxins, or the addition of biologics and pharmaceuticals. Such conduits may interface with a sufficiently rigid body for maintaining a desired shape, where rigid portions are connected to a porous membrane for performing the aforementioned filtering or delivery of a substance. For example, an implantable conduit may include a porous membrane placed between, and affixed to, substantially rigid end portions. Often, the interface(s) between the porous membrane and other portions of the implantable conduit can be problematic. For example, these interfaces can be susceptible to material build-up, loosening or breaking, the formation of relatively sharp edges, and so on. There remains a need for improved fluid conduits, e.g., fluid conduits lacking such interfaces.

SUMMARY

In an aspect, a fluid conduit disclosed herein may include a first portion having a first porosity, a second portion disposed immediately adjacent to the first portion and having a second porosity that is greater than the first porosity, and a third portion disposed immediately adjacent to the second portion, the third portion having a third porosity that is less than the second porosity. Each of the first portion, the second portion, and the third portion may be integrally formed as a single, continuous piece defining the fluid conduit.

Implementations may include one or more of the following features. The first portion, the second portion, and the third portion may be formed using the same material such that they are continuous across the fluid conduit. The fluid conduit may consist of the first portion, the second portion, and the third portion. The fluid conduit may be shaped and sized to be implantable within a patient. One or more of the first portion and the third portion may be sized and shaped for anastomosis into a blood vessel of the patient. The first portion may have a first stiffness, the second portion may have a second stiffness that is less than the first stiffness, and the third portion may have a third stiffness that is greater than the second stiffness. The fluid conduit may be shaped and sized to be implantable within a patient, where one or more of the first stiffness and the third stiffness is suitable for anastomosis of one or more of the first portion and the third portion with a blood vessel of the patient. The fluid conduit may further include a device for delivering a therapeutic substance to a patient. The fluid conduit may be sized and shaped to permit one or more of ultrafiltration and dialysis. The first portion, the second portion, and the third portion may be formed using one or more of a single electrospinning process or a single extrusion process. The fluid conduit may lack interfaces between the first portion, the second portion, and the third portion. A material used to form the fluid conduit may include a therapeutic agent.

In an aspect, a method disclosed herein may include forming a first portion of a fluid conduit during an electrospinning process using a first set of parameters such that the first portion includes a first porosity, where the electrospinning process includes extruding a material from a spinneret, electrically charging the material, and receiving the electrically charged material on a collector. The method may also include forming a second portion adjacent to the first portion during the electrospinning process using a second set of parameters such that the second portion defines a membrane having a second porosity that is greater than the first porosity, and forming a third portion adjacent to the second portion during the electrospinning process using a third set of parameters such that the third portion includes a third porosity that is less than the second porosity.

Implementations may include one or more of the following features. The method may further include adjusting a spin rate of the collector to control one or more of the first porosity, the second porosity, and the third porosity. The method may further include adjusting a speed with which the spinneret and the collector move relative to one another to control one or more of the first porosity, the second porosity, and the third porosity. The method may further include adjusting a distance between the spinneret and the collector to control one or more of the first porosity, the second porosity, and the third porosity. The method may further include adjusting an extrusion rate from the spinneret to control one or more of the first porosity, the second porosity, and the third porosity. The first portion may include a first stiffness, the membrane of the second portion may include a second stiffness that is less than the first stiffness, and the third portion may include a third stiffness that is greater than the second stiffness. The electrospinning process may use a build material including polyethylene terephthalate. The build material may further include a therapeutic agent. The first set of parameters and the third set of parameters may be the same. The method may further include coating the collector with a therapeutic agent prior to beginning the electrospinning process.

In an aspect, a method disclosed herein may include extruding a first build material in an additive manufacturing process to form a first portion of a fluid conduit including a first porosity, and selectively adding a second build material to the first build material during the additive manufacturing process to form a second portion adjacent to the first portion, the second build material including one or more pore-formers such that the second portion defines a membrane having a second porosity that is greater than the first porosity.

Implementations may include one or more of the following features. The method may further include extruding the first build material in the additive manufacturing process to form a third portion adjacent to the second portion, the third portion including a third porosity that is less than the second porosity. The first portion may include a first stiffness, the membrane of the second portion may include a second stiffness that is less than the first stiffness, and the third portion may include a third stiffness that is greater than the second stiffness. The fluid conduit may be shaped and sized to be implantable within a patient. The fluid conduit may be shaped and sized for use in a dialyzer.

These and other features, aspects, and advantages of the present teachings will become better understood with reference to the following description, examples, and appended claims.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein. In the drawings, like reference numerals generally identify corresponding elements.

FIG. 6 is a flow chart of a method of making a fluid conduit, in accordance with a representative embodiment.

DETAILED DESCRIPTION

Figure 1:
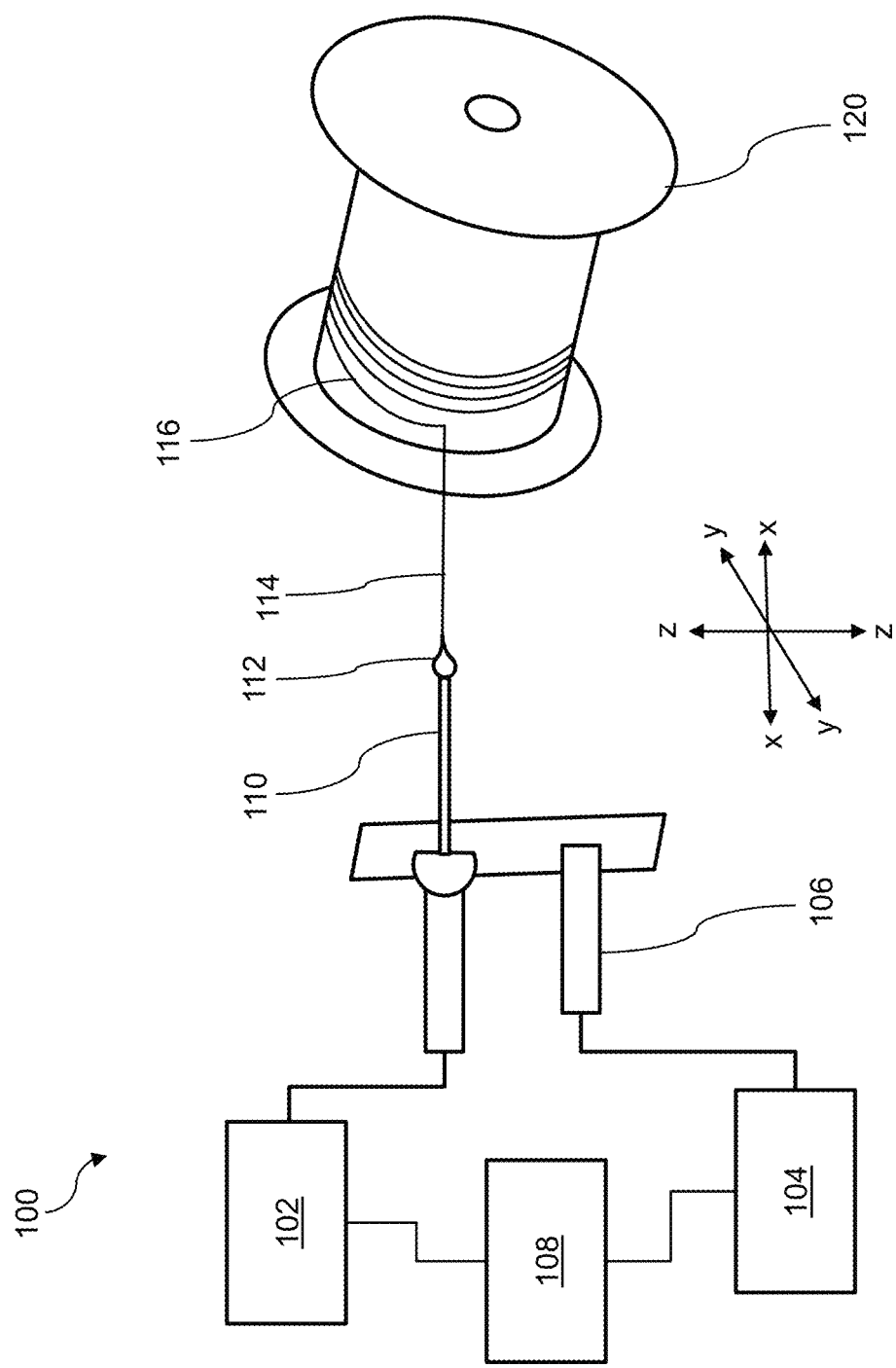
FIG. 1 illustrates an electrospinning system, in accordance with a representative embodiment.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "about," "approximately," or "substantially" when used in reference to physical characteristics, should be understood to contemplate a range of deviations that would be appreciated by one of ordinary skill in the art to operate satisfactorily for a corresponding use, function, purpose, or the like. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms unless specifically stated to the contrary.

In general, the devices, systems, and methods disclosed herein relate to a fluid conduit, e.g., an implantable fluid conduit such as one for the selective removal of water and/or toxins from a patient, and/or for delivering a therapeutic substance to a patient. The fluid conduit may include portions (e.g., portions disposed at its ends) that are relatively non-porous and relatively strong mechanically, e.g., where these portions are suitable for anastomosis into a blood vessel. The fluid conduit may further include another portion (e.g., a portion disposed between non-porous, substantially rigid end portions) that is relatively porous, e.g., where this portion is a membrane portion suitable for filtration (e.g., ultrafiltration) and/or for delivering a therapeutic substance to a patient. Despite the different characteristics between the different portions of the fluid conduit, the fluid conduit itself may be constructed as a single piece during a single manufacturing process. That is, in certain implementations, the fluid conduit piece may be a continuous unitary piece such that there are no interfaces, connections, grafts, glues, joints, step changes in the internal and/or external diameter, and so on between the different portions of the fluid conduit. The lack of such interfaces, or rather the construction of the fluid conduit as a single piece, may provide certain advantages including without limitation being cheaper/faster to manufacture, and mitigating the probability of clogging or clotting when blood flows through the fluid conduit. That is, the fewer obstructions, protrusions, indentations—e.g., "nooks and crannies"—in the fluid conduit, the lower the probability of clotting, clogging, breaking, undesired leaking, and so on. A manufacturing technique for creating such a single-piece fluid conduit may include electrospinning, although other manufacturing techniques are also or instead possible as will be apparent to one skilled in the art (e.g., three-dimensional printing or other additive manufacturing, casting, melt spinning, pore forming using a solvent or the like, gamma ray manufacturing, and so on). As discussed herein, a fluid conduit according to the present teachings may be used for ultrafiltration—that is, the removal of water and/or other solutes (e.g., solutes smaller than albumin, other relatively small molecules, and so on) from a patient's blood and/or other tissue via mechanical or chemical means. Thus, in general, a fluid conduit described herein may include a single bore bifunctional conduit with a microporous segment between two non-porous segments for anastomosis of the conduit to the vasculature.

The fluid conduit described herein may represent an improvement to one or more of the devices described in U.S. Pat. Nos. 8,241,239 and 9,138,521, where the entire contents of each are hereby incorporated by reference. Thus, the fluid conduit described herein may include an implantable ultrafiltration device (e.g., made of semi-permeable hollow fiber(s)) contained within a cartridge anastomosed to the vasculature, and the use of an implanted pump to actively control and transfer the ultrafiltrate that permeates the fluid conduit to the bladder of a patient. To simplify these devices, however, the fluid conduit described herein may be bifunctional with a designated porous segment (to permit ultrafiltrate transport) between two non-porous segments to anastomose the device to the arterial/venous circulation. This single bifunctional conduit may offer several distinct advantages including without limitation the elimination of multiple hollow fibers (or hollow fiber bundles), the elimination of bifurcated headers of the cartridge, and the elimination of connections formed of synthetic vascular grafts to the device cartridge for anastomosis to the vasculature. The fluid conduit described herein may also simplify assembly and manufacturing, where an implantable pump may be used to control the ultrafiltrate flow rate and the transfer of the fluid to the patient's bladder. Thus, in certain implementations, the present teachings may include one or more of: a bifunctional tubular conduit, an implantable biocompatible cartridge to house the bifunctional conduit and collect the ultrafiltrate, and an ultrafiltration pump and catheter to transport the ultrafiltrate to the bladder of a patient.

By way of example, the fluid conduit described herein may include a hollow fiber for use in a dialyzer, and/or the fluid conduit may be used to supplement or replace components of a dialyzer. That is, a fluid conduit according to the present teachings may include one or more substantially porous sections in combination with one or more substantially non-porous sections (which may also or instead be relatively rigid compared to the aforementioned porous sections), but where the fluid conduit lacks any cumbersome connection interfaces between different sections. In this manner, the one or more substantially non-porous sections may be used as a substitute for traditional potted ends that are found on the hollow fibers of dialyzers.

As discussed above, a manufacturing technique for creating a single-piece fluid conduit according to certain implementations may include electrospinning. Thus, a brief description of electrospinning will be provided for context with reference to FIG. 1.

FIG. 1 illustrates an electrospinning system, in accordance with a representative embodiment. In general, the electrospinning system 100 may be used for fiber production, where an electric force draws charged threads of polymer solutions (or polymer melts) up to fiber diameters sufficient for a desired application. As shown in the figure, a typical system 100 for an electrospinning process may include, amongst other things, a material source 102, a power supply 104, a voltage applicator 106, a controller 108, a spinneret 110, and a collector 120.

The material source 102 may contain a polymer solution, a polymer melt, or other material, for controllably supplying the material to the spinneret 110. As discussed herein, the material may include a single material or a blend of materials (e.g., a blend of polymers). In some applications, the material source 102 may include one or more of a syringe, an injection pump (or other pump), a container, and the like. A variable or parameter that can be controlled in the system 100 may include the type of material, a concentration of the material or another controllable material property, a flow rate of the material fed to the spinneret 110, and so on. In this manner, the material source 102 or a component thereof may be coupled to the controller 108 as explained below.

The power supply 104 may include a high-voltage, direct current (DC) power supply. The power supply 104 may apply a predetermined voltage to the system 100 to create an electric field between a tip of the spinneret 110 and the collector 120, e.g., using the voltage applicator 106. The electric field may be created by a voltage difference between the spinneret 110 and the collector 120. A variable or parameter that can be controlled in the system 100 may include the voltage that is applied by the power supply 104, or otherwise controlling the electric field that is created. In this manner, the power supply 104 and voltage applicator 106 may be coupled to the controller 108 as explained below.

The controller 108 may control one or more of the components of the system 100, and therefore one or more of the parameters of the system 100. The controller 108 may include, or otherwise be in communication with, a processor and a memory. The controller 108 may be electronically coupled (e.g., wired or wirelessly) in a communicating relationship with one or more of the components of the system 100. Thus, in an implementation, the controller 108 may include a processor and a memory, where the processor is configured to control one or more of the material source 102 (or component thereof), the power supply 104, the voltage applicator 106, the spinneret 110, the collector 120, and so on.

As discussed above, the controller 108 may be operable to control the components of the system 100, where the controller 108 may include any combination of software and/or processing circuitry suitable for controlling the various components of the system 100 described herein including without limitation processors, microprocessors, microcontrollers, application-specific integrated circuits, programmable gate arrays, and any other digital and/or analog components, as well as combinations of the foregoing, along with inputs and outputs for transceiving control signals, drive signals, power signals, sensor signals, and the like. In certain implementations, the controller 108 may include the processor or other processing circuitry with sufficient computational power to provide related functions such as executing an operating system, providing a graphical user interface (e.g., to a display coupled to the controller 108 or another component of the system 100), set and provide rules and instructions for operation of a component of the system 100, convert sensed information into instructions, and operate a web server or otherwise host remote operators and/or activity through a communications interface. In certain implementations, the controller 108 may include a printed circuit board, an Arduino controller or similar, a Raspberry Pi controller or the like, a prototyping board, or other computer-related components.

The spinneret 110 may dispense the material out of a tip thereof. The spinneret 110 may include one or more needles (e.g., the needle of a hypodermic syringe), one or more nozzles, or other extrusion tip(s) in fluid communication with the material source 102, e.g., in fluid communication with any pumps contained therein or therebetween. A variable or parameter that can be controlled in the system 100 may include the rate at which the material is extruded from the spinneret 110, and movement of the spinneret 110 along one or more of an x-axis, a y-axis, and a z-axis, e.g., relative to the collector 120.

The collector 120 may include a grounded collector such as a spindle as shown in the figure, or another form of a collector plate. The collector 120 may be rotatable or otherwise movable to collect the material extruded from the spinneret 110. A variable or parameter that can be controlled in the system 100 may include the rate at which the collector 120 spins or moves to collect fibers formed in the electrospinning process, and movement of the collector 120 along one or more of an x-axis, a y-axis, and a z-axis. In this manner, relative movement of the spinneret 110 and the collector 120 may be controlled, e.g., by the controller 108.

In an electrospinning process, e.g., using the system 100 shown in the figure, when a sufficiently high voltage is applied to a liquid droplet 112, the body of the droplet 112 becomes charged, and internal electrostatic repulsion counteracts the surface tension and stretches the droplet 112 to form a stream 114. Simultaneously, the droplet 112 is brought into close proximity with a grounded or oppositely-charged collector 120, which electrostatically attracts the droplet 112.

At a critical point the droplet structure collapses entirely under these electrostatic forces, becoming the stream 114 of liquid erupting from the spinneret 110 towards the collector 120—e.g., forming a "Taylor cone." If the molecular cohesion of the liquid is sufficiently high, stream breakup does not occur in flight. As the stream dries in flight, the mode of current flow changes from ohmic to convective as the charge migrates to the surface of the fiber. The jet is then elongated by a whipping process caused by electrostatic repulsion initiated at small bends in the fiber, until it is finally deposited on the grounded collector 120 (e.g., a spindle). The elongation and thinning of the fiber resulting from this bending instability leads to the formation of substantially uniform fibers 116 with nanometer-scale diameters. The fibers 116 manufactured via electrospinning may include one or more hollow fibers, tubes, or conduits, e.g., by controlling certain parameters of the electrospinning process (e.g., the extrusion rate of the material from the spinneret 110, the rotation and/or translation rate of the collector 120), and through the selection and use of certain materials.

Figure 2:
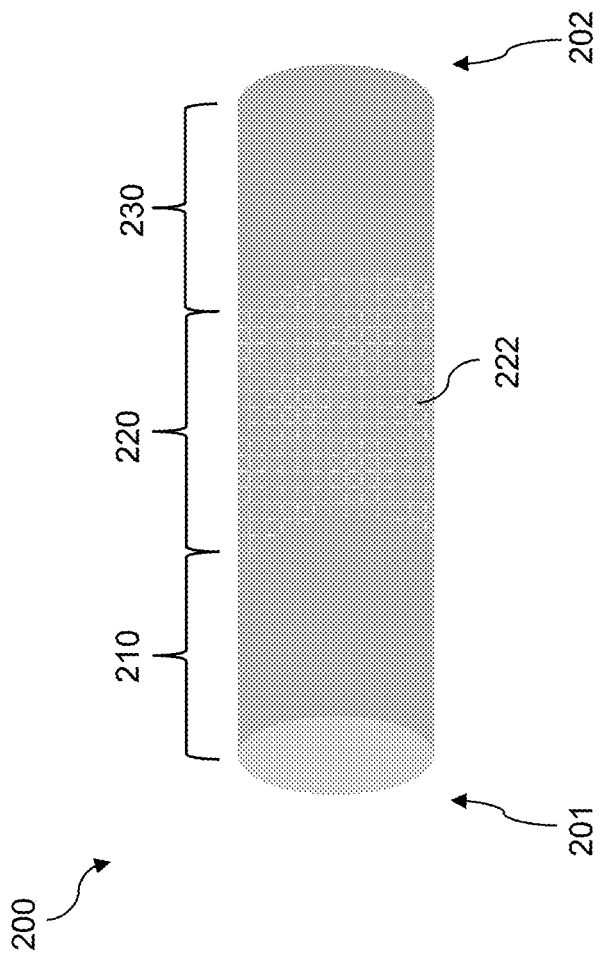
FIG. 2 illustrates a fluid conduit, in accordance with a representative embodiment.

FIG. 2 illustrates a fluid conduit, in accordance with a representative embodiment. As discussed herein, the fluid conduit 200 may include substantially non-porous and mechanically strong ends such that the fluid conduit 200 is suitable for anastomosis into a blood vessel, and one or more other portion(s) that are relatively porous, e.g., having a sufficient porosity for ultrafiltration. By way of example, substantially non-porous portions of the fluid conduit 200 may be impermeable to fluid transfer through the material that forms these portions, or the porosity of these sections may have such a low porosity that it is essentially zero for most intended use cases. Despite the different characteristics of the different portions of the fluid conduit 200, the fluid conduit 200 itself may be constructed in a single piece, where there are no connections, grafts, glues, joints, and the like for connecting the different portions of the fluid conduit 200. Thus, the fluid conduit 200 may be made from one, single piece, e.g., in a single manufacturing operation. In some embodiments, the single manufacturing operation may enable the fluid conduit 200 to have a substantially uniform internal and/or external diameter, and/or a substantially smooth internal and/or external diameter (i.e., but for pores in a porous section in some implementations). Also, or instead, any transitions between diameter changes in the fluid conduit 200 may be relatively smooth or non-abrupt. That is, in some embodiments, the single manufacturing operation may also prevent a step change in the internal and/or external diameter of the fluid conduit 200. By way of further example, the internal diameter of the fluid conduit 200 may be about 6 mm, which may be consistent throughout its length.

The fluid conduit 200 may include at least three portions as shown in the figure—e.g., a first portion 210, a second portion 220, and a third portion 230. The first portion 210 and the third portion 230 may generally be non-porous and mechanically strong for providing support to the structure of the fluid conduit 200, and the second portion 220 may generally be porous defining a porous membrane, e.g., so that the fluid conduit 200 can allow ultrafiltration through the second portion 220. Thus, the fluid conduit 200 may be shaped and sized to be implantable within a patient. Specifically, one or more of the first portion 210 and the third portion 230 may be sized and shaped for anastomosis into a blood vessel of the patient, and the third portion 230 may be sized and shaped for one or more of ultrafiltration or delivering a therapeutic substance to the patient. Thus, the fluid conduit 200 may be part of, and may be included in, a system or device for delivering a therapeutic substance to a patient or for allowing ultrafiltration—see, e.g., FIG. 3 described below. Such a system or device including the fluid conduit 200 may be disposed (at least partially) internal or external to a patient. For example, the system or device may include a housing for the fluid conduit 200, where the housing is portable (e.g., wearable) and disposed substantially external to the patient's anatomy.

In certain implementations, the fluid conduit 200 may also or instead be configured for use in a dialyzer or a dialysis system. For example, the second portion 220 of the fluid conduit 200 may form a semipermeable membrane, where the first portion 210 and the third portion 230 form relatively impermeable ends configured to be engaged with support structures or the like. By way of example, the first portion 210 and the third portion 230 may be structurally configured to be potted into glue or the like, where a decreased porosity of these portions relative to the second portion 220 is advantageous such that the glue or the like does not infiltrate an interior of the fluid conduit 200 or otherwise contaminate a dialysis system. In such a dialyzer, blood may flow in one direction where the dialysate flows in the opposite direction. The fluid conduit 200 may be used as one or more of the hollow fibers contained in the dialyzer, e.g., where a dialyzer may include thousands of such hollow fibers. In the dialyzer, blood may flow into one end and through the hollow fibers; at the same time, dialysate may be pumped into the dialyzer and across the hollow fibers. The fluid conduit 200 may also or instead be used in a parallel plate type of dialyzer, where the second portion 220 may be used as a semipermeable membrane that rests between grooves or ridges for the dialysate and the blood flow. Thus, generally, the fluid conduit 200 may be included as part of a dialysis system, where at least a portion of the dialysis system including the fluid conduit 200 may be disposed internal or external to a patient. For example, the dialysis system may include a housing for the fluid conduit 200, where the housing is portable (e.g., wearable) and disposed substantially external to the patient's anatomy.

The first portion 210 of the fluid conduit 200 may be disposed on a first end 201 of the fluid conduit 200, e.g., such that the first portion 210 defines the first end 201 of the fluid conduit 200. The first portion 210 may have a first stiffness and a first porosity. The first stiffness may be selected to provide sufficient rigidity to the fluid conduit 200 (e.g., the first end 201 of the fluid conduit 200), e.g., for anastomosis into a blood vessel of a patient. That is, the stiffness of the first portion 210 (or another portion of the fluid conduit 200 that is structurally configured for anastomosis into a blood vessel of an animal) may be the same as or similar to the stiffness found in commercially available vascular grafts. By way of example, the first portion 210 may have a Young's modulus as high as about 21 MPa (or greater in some implementations). More generally, non-porous portions of the fluid conduit 200 may have a greater stiffness than porous portions of the fluid conduit 200. Regarding porosity, the first porosity of the first portion 210 may, in fact, be substantially non-porous. Thus, the first portion 210 may be substantially non-porous.

The second portion 220 of the fluid conduit 200 may be disposed immediately adjacent to the first portion 210 and the third portion 230. That is, the second portion 220 may be disposed between the first portion 210 and the third portion 230. In certain implementations, the second portion 220 is disposed in the middle of the fluid conduit 200.

The second portion 220 may have a second stiffness that is less than the first stiffness and a second porosity that is greater than the first porosity. In this manner, the second portion 220 may define a porous membrane for the fluid conduit 200. As discussed herein, the fluid conduit 200 may be sized and shaped to permit ultrafiltration. In this manner, the second portion 220 may be sized and shaped to permit ultrafiltration, e.g., by having a sufficient pore size to permit ultrafiltration. In other words, the size of the pores 222 of the second portion 220 may be specifically selected to permit ultrafiltration. For example, the pore size for ultrafiltration may range between about 0.002 microns to about 0.1 microns and have a molecular weight cutoff range between about 10 kDa to about 150 kDa. The pore size and molecular weight cutoff range of the second portion 220 may be selected depending on the desired molecule retention.

In some implementations, the porosity of the second portion 220 may have a molecular weight cutoff of about 65-70 kDa. That is, for example, the majority of molecules in a patient's blood smaller than about 65-70 kDa may pass through the pores 222 of the second portion 220 producing ultrafiltrate. Such molecules may include, for example, urea (about 60 kDa), creatinine (about 113 kDa), phosphate (about 134 kDa), vitamin B12 (about 1355 kDa), vancomycin (about 1448 kDa), insulin (about 5200 kDa), endotoxin fragments (about 1000-15000 kDa) (i.e., for removal of these fragments), parathyroid hormone (about 9425 kDa), beta-2-microgobulin (about 11818 kDa), myoglobin (about 17000 kDa), retinol-binding protein (about 21000 kDa), erythropoietin (EPO) (about 34000 kDa), and transferrin (about 9000 kDa). Molecules such as albumin (about 66000 kDa) may be substantially retained (e.g., about 90% or greater retention) in the patient's blood and prevented from passing through the pores 222 of the second portion 220. In some implementations, the porosity of the second portion 220 may have a molecular weight cutoff greater than about 70 kDa (e.g., about 80 kDa, 90 kDa, 100 kDa, 125 kDa, or 150 kDa) so molecules such as albumin and other larger proteins may also pass through the pores 222 of the second portion 220 producing ultrafiltrate. In some implementations, the porosity of the second portion 220 may be selected to have a molecular weight cutoff less than about 65 kDa (e.g., about 60 kDa, 50 kDa, 40 kDa, 30 kDa, 20 kDa, 15 kDa, or 10 kDa) so select molecules smaller than albumin may also be retained in the fluid conduit 200.

It will be understood that, however, in principle, there may be no limit on the porosity of the second portion 220 besides the manufacturing capabilities, but in one application only sufficient porosity for ultrafiltration may be desirous. In some implementations, the size of the pores 222 may be selected to allow for microfiltration and/or nanofiltration. In some implementations, the size of the pores 222 of the second portion 220 may also or instead be specifically selected to permit delivery of a therapeutic agent.

The third portion 230 of the fluid conduit 200 may be disposed immediately adjacent to the second portion 220. In certain implementations, the third portion 230 may be disposed on a second end 202 of the fluid conduit 200, e.g., such that the third portion 230 defines the second end 202 of the fluid conduit 200.

The third portion 230 may have a third stiffness that is greater than the second stiffness and a third porosity that is less than the second porosity. Similar to the first stiffness of the first portion 210, the third stiffness may be selected to provide sufficient rigidity to the fluid conduit 200 (e.g., the second end 202 of the fluid conduit 200), e.g., for anastomosis into a blood vessel of a patient. Also, similar to the first porosity of the first portion 210, the third porosity may, in fact, be substantially non-porous. Thus, the third portion 230 may be substantially non-porous. In this manner, in certain aspects, the first stiffness and the third stiffness are substantially equal, and the first porosity and the third porosity are substantially equal. One or more of the first stiffness and the third stiffness, and the first porosity and the third porosity, may instead be different.

As discussed herein, each of the first portion 210, the second portion 220, and the third portion 230 may be integrally formed as a single, continuous piece defining the fluid conduit 200. For example, the first portion 210, the second portion 220, and the third portion 230 may be formed using the same material (which may be a single material or a blend of materials) such that these portions are continuous across the fluid conduit 200. In other words, in certain implementations, the fluid conduit 200 may only consist of the first portion 210, the second portion 220, and the third portion 230, and nothing more—i.e., no other portions, connections, joints, bridges, glues, and so on. Thus, the fluid conduit 200 may lack interfaces between the first portion 210, the second portion 220, and the third portion 230.

The fluid conduit 200 may be made of only one material. In other words, the first portion 210, the second portion 220, and the third portion 230 may be made of the same material. In some aspects, a material used to form the fluid conduit 200 includes a therapeutic agent—e.g., a therapeutic agent may be embedded therein, or the material may otherwise contain therapeutic properties. The fluid conduit 200 being made of only one material, and/or the use of a therapeutic agent, may aid in mitigating neointimal hyperplasia or similar. For example, a material used to form the fluid conduit 200 may include one or more of an anticoagulant agent, an anticlotting agent, an anti-stenosis agent, an anti-platelet agent, and a hyperplasia agent. By way of further example, the fluid conduit 200 may include one or more pharmacologic agents such as everolimus, sirolimus, paclitaxel, heparin, and the like. In certain implementations, a material used to form the fluid conduit 200 includes a coloring agent. In this manner, one or more of the first portion 210, the second portion 220, and the third portion 230 may be identified using the coloring agent.

The material used to form the fluid conduit 200 (or at least a portion of the fluid conduit 200) may include one or more of polytetrafluoroethylene (PTFE), polyethylene terephthalate (PET, also known as polyester or Dacron®), or another material found in commercially available vascular grafts, and similar materials. In some embodiments, the material used to form the fluid conduit 200 (or at least a portion of the fluid conduit 200) may include one or more of cellulose triacetate (CTA), polysulfone (PS), polyethersulfone (PES), polymethylmethacrylate (PMMA), polyester polymer alloy (PEPA), ethylene vinyl alcohol copolymer (EVAL), polyacrylonitrile (PAN), polyvinylidene difluoride (PVDF), or another material found in commercially available hollow fiber membranes, and similar materials.

In certain implementations, the first portion 210, the second portion 220, and the third portion 230 are formed using a single manufacturing process, e.g., a single electrospinning process. The electrospinning process may be any as described herein, e.g., where an electrically charged polymer or other build-material is extruded across a gap and electrostatically attracted to an oppositely-charged collector (e.g., spindle) that provides the base for the structure being formed. Using such a manufacturing technique (or similar techniques), the porosity of the resultant structure may be relatively easy to control.

For example, the first portion 210 may be formed using the electrospinning process under certain conditions or using certain parameters such that the first portion 210 includes the first stiffness and first porosity. Then, during the same electrospinning process, the conditions or parameters may be adjusted to form the second portion 220 such that the second portion 220 includes the second stiffness and second porosity. Finally, during the same electrospinning process, the conditions or parameters may be adjusted yet again to form the third portion 230 such that the third portion 230 includes the third stiffness and third porosity. In this manner, the fluid conduit 200 may include an implantable electrospun conduit.

Other manufacturing processes may also or instead be used to form the first portion 210, the second portion 220, and the third portion 230. For example, an additive manufacturing process may be used, where the first portion 210 and the third portion 230 are extruded using a first build material, and where the second portion 220 is formed by selectively adding pore-formers or the like to the first build material when forming the second portion 220.

Figure 3:
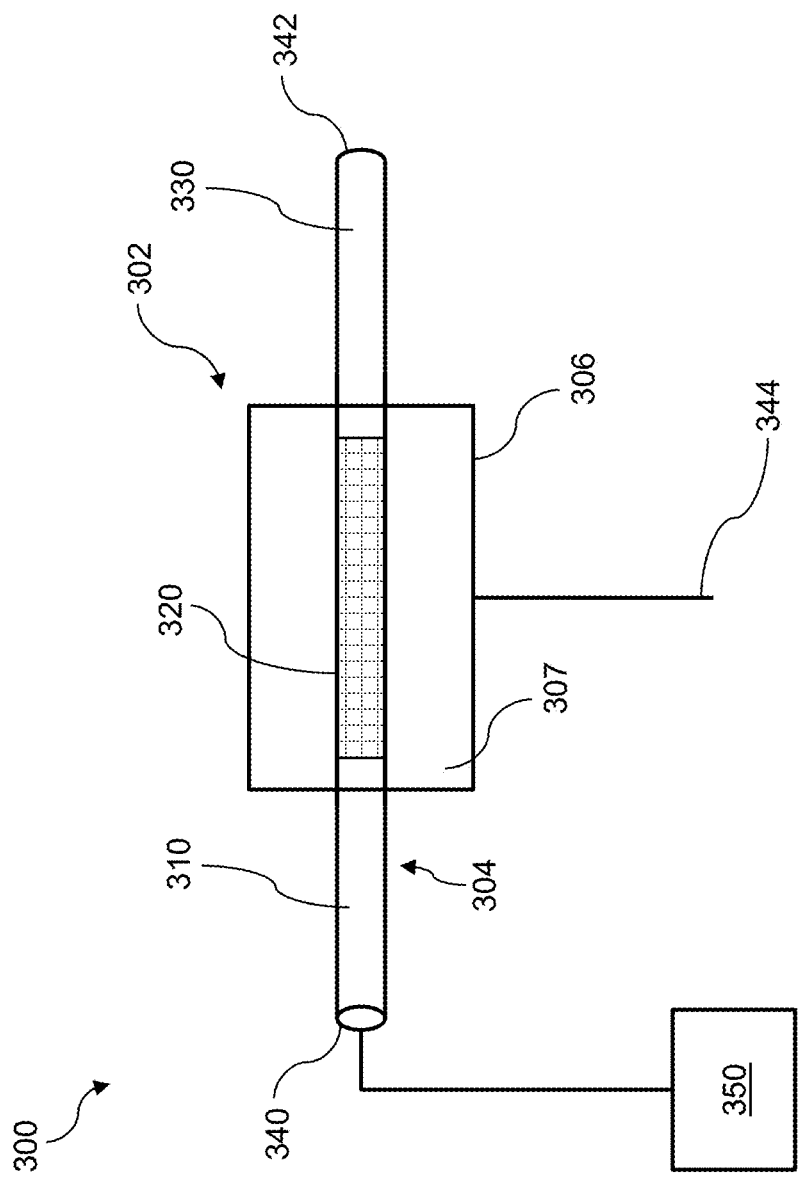
FIG. 3 illustrates a therapeutic system including a fluid conduit, in accordance with a representative embodiment.

FIG. 3 illustrates a therapeutic system including a fluid conduit, in accordance with a representative embodiment. The system 300 may generally include a device 302 and a fluid conduit 304 at least partly disposed within or connected to the device 302.

The device 302 may be configured for delivering a therapeutic substance to a patient, e.g., one or more of a pharmaceutical and a biologic. The device 302 may also or instead include a dialysis system or machine, or part of a dialysis system (e.g., a dialyzer). In this manner, the fluid conduit 304 may be structurally configured for performing one or more of ultrafiltration and dialysis. The device 302 may include an inlet 340 (e.g., defined by the first portion 310 of the fluid conduit 304), an outlet 342 (e.g., defined by the third portion 330 of the fluid conduit 304), and a drain 344. The device 302 may be structurally configured for external or internal use relative to a patient's anatomy, wholly or partially.

The fluid conduit 304 may be the same or similar to other fluid conduits described herein, e.g., the fluid conduit 200 described above with reference to FIG. 2. Thus, the fluid conduit 304 may include a first portion 310, a second portion 320, and a third portion 330. The first portion 310 and the third portion 330 may generally include a stiffness that is greater than the stiffness of the second portion 320, and the second portion 320 may generally include a porosity that is greater than that of the first portion 310 and the third portion 330. The fluid conduit 304 may be formed as a single piece as described herein.

As shown in the figure, the device 302 may include a housing 306. The housing 306 may be machined, molded, or otherwise fabricated, where connections and sterilization (e.g., using ethylene oxide) will be included in the device 302 or housing 306. In certain implementations, the housing 306 may include a reusable or disposable cartridge or the like. The housing 306 may also or instead be configured to be portable with a patient, e.g., wearable by the patient. By way of example, the housing 306 may be structurally configured for coupling to a patient's body or clothing, e.g., a belt or strap to be worn by the patient. As shown in the figure, the second portion 320 may be substantially contained within the housing 306, and the first portion 310 and the third portion 330 may be substantially disposed external to the housing 306. The first portion 310 may define an inlet 340 for the device 302, and the second portion 320 may define an outlet 342 for the device 302. Thus, in some aspects, the second portion 320 defines an ultrafiltration membrane that is at least partially (e.g., fully) contained within the housing 306. In this manner, the device 302 may represent a simpler and cleaner way of implementing an implantable ultrafiltration device rather than a typical device in the art that uses separate sections for the inlet/outlet and the ultrafiltration membrane.

The system 300 or device 302 may be used with an implantable pump 350 or the like. In some implementations, the pump 350 may be controllable to change a pressure gradient within the device 302 for ultrafiltration. In some cases, the pressure gradient can be reversed, and the same system 300 or device 302 may thus be used for the delivery of a therapeutic agent, to house immobilized stem cells and function as a bioreactor, and the like. Although the pump 350 is shown in fluid communication with inlet 340, the pump could alternatively or additionally be in fluid communication with the outlet 342, drain 344, or the internal volume 307 of the device 302.

The pump 350 may include a subcutaneously implanted battery powered pump to transfer the ultrafiltrate to the bladder of the patient via the fluid conduit 304. The pump 350 may also or instead be configured for controlled, continuous, slow removal of fluid from the abdominal cavity in patients with refractory ascites. The pump 350 may be charged inductively through the skin using a wireless handheld charging device. Fluid may be pumped to a patient where it is excreted naturally from the body. The pump 350 may be programmed and adjusted to the medical needs of the patient, and can be reprogrammed at any time after implant using a computing device.

Using a pump 350 and a fluid conduit 304 as described herein may provide several advantages, some of which are listed below by way of example. For example, by actively controlling an ultrafiltration rate applying an adjustable transmembrane pressure, higher and more consistent ultrafiltration rates may be achieved compared to using a control valve. Also, the pump 350 may aid active transfer of the ultrafiltrate to the patient. Moreover, the ability to monitor and adjust the pump 350 may enable patient-tailored control of the ultrafiltration flow rate including establishing higher transmembrane pressure. Achieving higher and more consistent ultrafiltration rates may enable a reduction in the membrane surface area needed.

The system 300 may also or instead include a housing 306 containing multiple fluid conduits 304 (e.g., relatively large bore hollow fiber membranes) connected to a patient's vascular system (e.g., femoral artery and vein) using synthetic vascular grafts. In this manner, ultrafiltrate removed by the device 302 may be directed to the patient's bladder via a catheter or the like. A valve or a pump 350 may control the ultrafiltrate flow rate and the removal of fluid from the patient. The device 302 may be surgically implanted to allow for continuous blood flow and fluid removal with ambulatory freedom.

Some characteristics of the system 300 may include having a daily mean ultrafiltration volume of up to about 1.5 liters with a mean ultrafiltration rate of approximately 1 ml/min, or an ultrafiltration volume of up to about 3 liters per 24 hours with a ultrafiltration rate of about 2.1 ml/min. The estimated mean transmembrane pressure may be about 50 to about 80 mmHg. As discussed above, the internal diameter of the fluid conduit 304 may be about 6 mm, and the porosity of the second portion 320 may have a molecular weight cutoff below about 70 kDa.

The system 300 or device 302 may be used for one or more of the following applications, which are provided by way of example: ultrafiltration to remove fluid from the vasculature or otherwise from a patient, to deliver biologics (e.g., by housing cells within the internal volume 307), and for delivering drugs or a fluid from the internal volume 307 through the membrane defined by the second portion 320 (i.e., reversed ultrafiltration) using a pump 350. Also, drugs (e.g., anticoagulant, and anti-stenosis/hyperplasia agents) could be included in the wall of the fluid conduit 304 during its manufacturing.

The system 300, device 302, or fluid conduit 304 may also or instead be used for treating patients suffering from fluid overload or excess fluid retention that may be the result of cardiac or renal disease. For example, heart failure and chronic kidney disease patients with fluid overload may benefit from the system 300, device 302, or fluid conduit 304. Some other examples of uses for a fluid conduit 304 as described herein are provided below.

In patients with congestive heart failure (CHF) and acute decompensated heart failure (ADHF), isolated ultrafiltration using the fluid conduit 304 may relieve congestive symptoms and improve loop diuretic responsiveness. In end stage renal disease (ESRD) patients, having a gentle continuous option of fluid removal could avoid fluid accumulation, and also lead to more uniform control of blood pressure and left ventricular remodeling. So, the fluid conduit 304 could be used in ESRD patients, and especially patients who have fluid overload, have signs/symptoms of congestive heart failure, and are refractory to standard treatments. In chronic kidney disease patients, a fluid conduit 304 could help treat hypervolemia, control hypertension, and can delay the initiation of dialysis.

Thus, the devices, systems, and methods described herein may include fluid management to treat or prevent fluid overload. Eliminating or preventing hypervolemia could improve a patient's quality of life by reducing hospitalization (length of stay and readmissions) for fluid overload in heart failure patients with volume overload and diuretic resistance, reducing cardiovascular disease events, reducing hypertension and antihypertension medications, reducing isolated ultrafiltration, reducing hemodynamic instability and possibly reducing hypotension episodes during dialysis, and reducing fluid restrictions and fatigue, e.g., from severe thirst.

Figure 4:
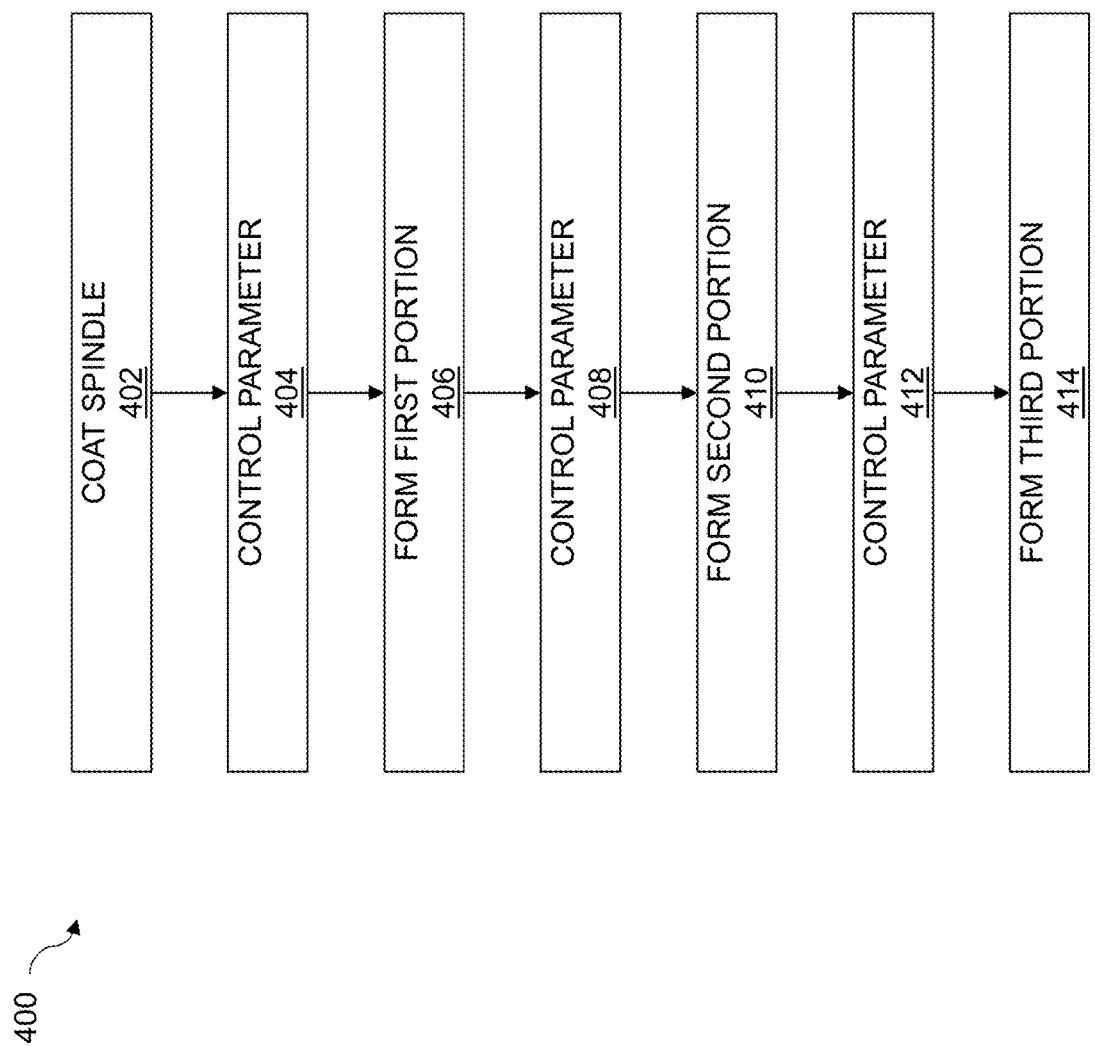
FIG. 4 is a flow chart of a method of making a fluid conduit, in accordance with a representative embodiment.

FIG. 4 is a flow chart of a method of making a fluid conduit, in accordance with a representative embodiment. Specifically, the method 400 may include a process for making any of the fluid conduits described herein, e.g., those shown in FIGS. 1 and 2, described above. For example, the method 400 may include making a fluid conduit using an electrospinning process including extruding a material from a spinneret, electrically charging the material, and receiving the electrically charged material on a collector (e.g., a spindle).

As shown in step 402, the method 400 may include coating the collector with a therapeutic agent as described above prior to beginning the electrospinning process (or as an interstitial step between different parts of the electrospinning process). Also, or instead, the collector may be coated or engaged with other materials or substances. By way of example, the collector may be coated or covered with particulates that promote the formation of porous segments when fabricating one or more portions of a fluid conduit (e.g., a substantially porous portion). In some implementations, this coating or covering can be selectively removed for the fabrication of substantially non-porous portions of the fluid conduit.

As shown in step 404, the method 400 may include controlling one or more parameters for the electrospinning process. For example, this step 404 may include setting one or more of a spin rate of the collector, a speed with which the spinneret and the collector move relative to one another, a distance between the spinneret and the collector, an extrusion rate from the spinneret, and so on. Each of these parameters can individually or collectively be controlled to produce a desired stiffness or porosity characteristic in the resultant conduit. For example, all other parameters being equal, individually increasing (a) the spin rate of the collector, (b) the speed with which the spinneret and the collector move relative to each other, or (c) the distance between the spinneret and the collector increases the porosity and decreases the stiffness of the resultant structure. On the other hand, increasing the extrusion rate behaves in the opposite direction, to decrease the porosity and increase the stiffness. Similarly, with all other parameters being equal, individually decreasing (a) the spin rate of the collector, (b) the speed with which the spinneret and the collector move relative to each other, or (c) the distance between the spinneret and the collector decreases the porosity and increases the stiffness of the resultant structure. On the other hand, decreasing the extrusion rate behaves in the opposite direction, to increase the porosity and decrease the stiffness.

As shown in step 406, the method 400 may include forming a first portion of a fluid conduit during the electrospinning process using a first set of parameters such that the first portion includes a first stiffness and a first porosity. The first set of parameters may be directly related to the parameters controlled in step 404 above.

As shown in step 408, the method 400 may include controlling one or more parameters for the electrospinning process, e.g., adjusting the parameters from the first set of parameters to a second set of parameters. Similar to the above, this may include adjusting one or more of a spin rate of the collector, a speed with which the spinneret and the collector move relative to one another, a distance between the spinneret and the collector, an extrusion rate from the spinneret, and so on, so that the desired stiffness/porosity conditions are achieved.

As shown in step 410, the method 400 may include forming a second portion adjacent to the first portion during the electrospinning process using a second set of parameters such that the second portion defines a membrane having a second stiffness that is less than the first stiffness and a second porosity that is greater than the first porosity.

As shown in step 412, the method 400 may include controlling one or more parameters for the electrospinning process, e.g., adjusting the parameters from the second set of parameters to a third set of parameters, so that the desired stiffness/porosity conditions are achieved. Similar to the above, this may include adjusting one or more of a spin rate of the collector, a speed with which the spinneret and the collector move relative to one another, a distance between the spinneret and the collector, an extrusion rate from the spinneret, and so on.

As shown in step 414, the method 400 may include forming a third portion adjacent to the second portion during the electrospinning process using a third set of parameters such that the third portion includes a third stiffness that is greater than the second stiffness and a third porosity that is less than the second porosity. The first set of parameters and the third set of parameters may be, but in general need not be, the same.

It will be understood that, as explained above, the parameters, characteristics, or settings of the electrospinning process may be controlled to form one or more of the first portion, the second portion, and the third portion of a fluid conduit such that the fluid conduit is made as one integral piece in a single electrospinning process. In this manner, and as explained above, controlling one or more of the first set of parameters, the second set of parameters, and the third set of parameters may include one or more of adjusting a spin rate of the collector, adjusting a speed with which the spinneret and the collector move relative to one another, adjusting a distance between the spinneret and the collector, adjusting an extrusion rate from the spinneret, and so on.

The build material may include an FDA-approved polymer or a blend of different polymers. For example, some materials that have a spider web-like composition can form a variety of unusual and difficult-to-manufacture shapes while also demonstrating improved healing properties after implantation as compared to other textile constructs. By way of example, a 6-mm nanofibrous conduit that shows targeted wicking capability may be used. The base polymer of the nanofibrous construct may include polyethylene terephthalate (PET, also known as polyester or Dacron®). This may be advantageous as electrospun PET has shown superior healing as compared to woven or knitted PET as well as ePTFE in various preclinical studies.

The electrospinning process may also or instead use a build material including one or more surface modifying materials or various co-polymers to modify the surface of the fluid conduit, e.g., to improve hemocompatibility as well as the incorporation of drugs or other bioactive agents directly into the nanofibers. This could be advantageous for localized drug elution (e.g., anticoagulation or anti-stenosis due to neointimal proliferation). The electrospinning process may be performed at room temperature, which can allow the incorporation of drugs or other bioactive agents directly into the nanofibers and the wall of the fluid conduit.

In addition to, or instead of, the electrospinning process described herein, an extrusion-based manufacturing process such as an additive manufacturing process may be used to form a fluid conduit as described herein. For example, during an additive manufacturing process, pore-formers or the like may be selectively added to a build material to control porosity—e.g., pore-formers may be selectively added to a build material to form the more-porous sections of the fluid conduit. Alternatively, an additive manufacturing process may switch between two different build materials to affect porosity, e.g., an additive manufacturing process may switch between a first build material lacking pore-formers and a second build material containing pore-formers.

Figure 5:
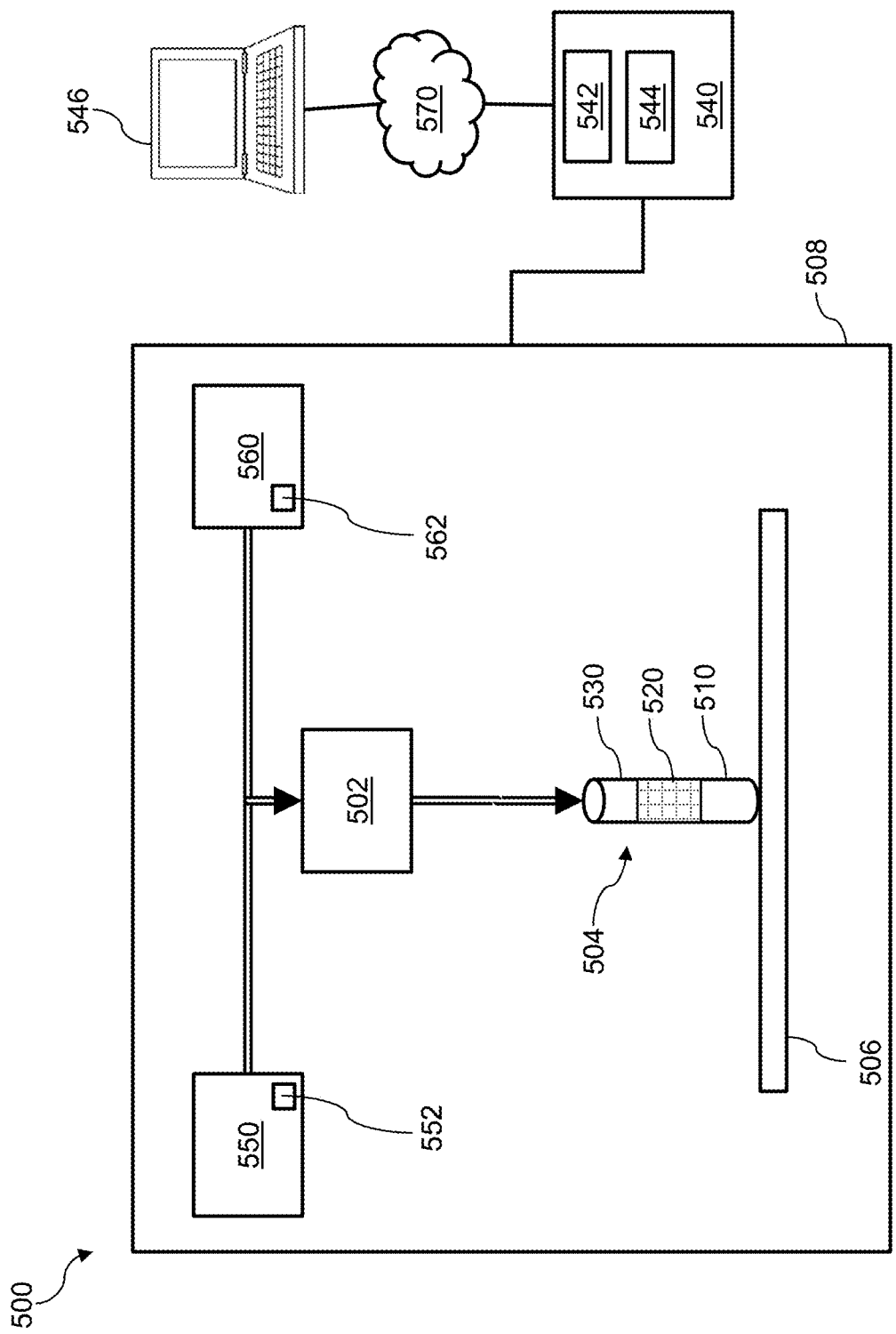
FIG. 5 illustrates an additive manufacturing system, in accordance with a representative embodiment.

FIG. 5 illustrates an additive manufacturing system, in accordance with a representative embodiment. The additive manufacturing system 500 may be configured for producing sub-millimeter diameter fibers or the like, e.g., which can be used in medical devices described herein such as for the hollow fibers contained in a dialyzer. The additive manufacturing system 500 may also or instead be used to form any other fluid conduit as described herein, where one such fluid conduit 504 is shown by way of representation in the figure.

Thus, the fluid conduit 504 may be the same or similar to other fluid conduits described herein, e.g., the fluid conduit 200 described above with reference to FIG. 2. In this manner, the fluid conduit 504 may include a first portion 510, a second portion 520, and a third portion 530. The first portion 510 and the third portion 530 may generally include a stiffness that is greater than the stiffness of the second portion 520, and the second portion 520 may generally include a porosity that is greater than that of the first portion 510 and the third portion 530. The fluid conduit 504 may be formed as a single piece as described herein.

The additive manufacturing system 500 shown in the figure may, for example, include a fused filament fabrication additive manufacturing system, or any other additive manufacturing system or combination of manufacturing systems including an extruder 502 that deposits one or more build materials to form the fluid conduit 504, e.g., according to a computerized model. For example, the additive manufacturing system 500 may include one or more build materials that are propelled by a drive system and heated to an extrudable state by a heating system, and then extruded through one or more nozzles. By concurrently controlling robotics to position the nozzle(s) along an extrusion path relative to a build plate 506, the fluid conduit 504 may be fabricated on the build plate 506 within a build environment 508, e.g., a controlled build environment 508 such as a heated chamber of a three-dimensional printer or the like. In general, a control system 540 may manage operation of the additive manufacturing system 500 to fabricate the fluid conduit 504.

The additive manufacturing system 500 may be configured for extrusion of one or more build materials to form the fluid conduit 504—e.g., a first build material 550 and a second build material 560. To this end, the extruder 502 may be configured for extrusion of the different build materials, or the additive manufacturing system 500 may include a separate extruder 502 or nozzle for each build material. The extruder 502 may also or instead be configured for extrusion of build materials having different additives or properties, e.g., different ratios of pore-formers 562 or the like contained therein.

The first build material 550 may be configured for forming the first portion 510 and the third portion 530 of the fluid conduit 504, and the second build material 560 may be configured for forming the second portion 520 of the fluid conduit 504. To this end, the second build material 560 may include one or more pore-formers 562. For example, the second build material 560 may include a mixture of the same material contained in the first build material 550, but with the one or more pore-formers 562 added thereto, or a higher ratio of pore-formers 562 contained therein relative to the first build material 550. In this manner, the control system 540 may be configured to selectively switch between the first build material 550 and the second build material 560 to form different portions of the fluid conduit 504. Also, or instead, the control system 540 may selectively add a controlled amount of the second build material 560 to the first build material 550 when forming different portions of the fluid conduit 504. In this manner, the second build material 560 may include pore-formers 562 for adding to the first build material 550, e.g., to form the second portion 520 of the fluid conduit 504.

In general, the build materials may have any shape or size suitable for extrusion in an additive manufacturing system 500 such as a fused filament fabrication process. For example, the build materials may be in pellet or particulate form for heating and compression, or the build materials may be formed as a wire (e.g., on a spool), a billet, or the like for feeding into an extrusion process. More generally, any geometry that might be suitably employed for heating and extrusion might be used as a form factor for a build material as contemplated herein. This may include loose bulk shapes such as spherical, ellipsoid, or flaked particles, as well as continuous feed shapes such as a rod, a wire, a filament, a spool, a block, or a volume of pellets.

One or more of the build materials may also or instead include a coloring agent 552, e.g., for identifying and distinguishing different portions of the fluid conduit 504. For example, a different coloring agent 552 may be used for the first portion 510 and the third portion 530 than that used when forming the second portion 520. In this manner, a user may be able to distinguish the second portion 520 from one or more of the first portion 510 and the third portion 530 of a fluid conduit 504.

In general, a control system 540 used in the additive manufacturing system 500 may include a controller or the like configured by computer executable code to control operation of one or more of the components of the additive manufacturing system 500. For example, the control system 540 may be operable to control the extruder 502, the build plate 506, robotics, drive systems, various temperature and pressure control systems, sensors, and any other components of the additive manufacturing system 500 described herein to fabricate the fluid conduit 504 from one or more of the first build material 550 and the second build material 560. The control system 540 may include any combination of software and/or processing circuitry suitable for controlling the various components of the additive manufacturing system 500 described herein including without limitation microprocessors, microcontrollers, application-specific integrated circuits, programmable gate arrays, and any other digital and/or analog components, as well as combinations of the foregoing, along with inputs and outputs for transceiving control signals, drive signals, power signals, sensor signals, and the like. In one aspect, the control system 540 may include a microprocessor or other processing circuitry with sufficient computational power to provide related functions such as executing an operating system, providing a graphical user interface (e.g., to a display coupled to the control system 540), converting three-dimensional models into tool instructions, and operating a web server or otherwise hosting remote users and/or activity through a network interface for communication through a network 570.

The control system 540 may include a processor 542 and memory 544, as well as any other co-processors, signal processors, inputs and outputs, digital-to-analog or analog-to-digital converters, and other processing circuitry useful for controlling and/or monitoring a fabrication process executing using the additive manufacturing system 500, e.g., by providing instructions to control operation of the extruder 502 or the like. To this end, the control system 540 may be coupled in a communicating relationship with a supply of one or more of the build materials, a drive system, a heating system, the extruder 502, the build plate 506, robotics, the build environment 508, and any other instrumentation or control components associated with the build process such as temperature sensors, pressure sensors, vacuum pumps, cameras, and so forth.

The control system 540 may generate machine-ready code for execution by the additive manufacturing system 500 to fabricate a fluid conduit 504 or another object from a three-dimensional model. In another aspect, the machine-ready code may be generated by an independent computing device 546 based on a three-dimensional model and communicated to the control system 540 through a network 570, which may include a local area network or an internetwork such as the Internet, and the control system 540 may interpret the machine-ready code and generate corresponding control signals to components of the additive manufacturing system 500. The control system 540 may also or instead deploy a number of strategies to improve the resulting fluid conduit 504, e.g., structurally.

FIG. 6 is a flow chart of a method of making a fluid conduit, in accordance with a representative embodiment. Specifically, the method 600 may include a process for making any of the fluid conduits described herein, e.g., those shown in FIGS. 2 and 5, described above. For example, the method 600 may include a process for making a fluid conduit that is shaped and sized to be implantable within a patient, and/or a fluid conduit that is shaped and sized for use in a dialyzer. The method 600 may include making a fluid conduit using an additive manufacturing process or another extrusion-based process.

As shown in step 602, the method 600 may include extruding a first build material in an additive manufacturing process to form a first portion of a fluid conduit. As described herein, the first portion may include a first stiffness and a first porosity.

As shown in step 604, the method 600 may include selectively adding a second build material to the first build material during the additive manufacturing process to form a second portion adjacent to the first portion. The second build material may include one or more pore-formers such that the second portion defines a membrane having a second stiffness that is less than the first stiffness and a second porosity that is greater than the first porosity. It will be understood that selectively adding the second build material to the first build material may include mixing the pore-former(s) with the first build material, and then extruding this mixture to form the second portion. Selectively adding the second build material to the first build material may also or instead include extruding the second build material, e.g., on a previously extruded layer that includes the first build material. One or more of the first build material and the second build material may include a coloring agent to identify one or more of the first portion and the second portion.

As shown in step 606, the method 600 may include extruding the first build material in the additive manufacturing process to form a third portion adjacent to the second portion. As described herein, the third portion may include a third stiffness that is greater than the second stiffness and a third porosity that is less than the second porosity.

In certain implementations, the second build material may be selectively added to the first build material during formation of one or more of the first portion and the third portion, i.e., in addition to, or instead of, during the formation of the second portion. In such implementations, a greater amount of the pore-former(s) may be added during the formation of the second portion than during the formation of the first portion and the third portion.

The same build material may be used for each of the first portion, the second portion, and the third portion of a fluid conduit as described herein. In some aspects, the build material further includes a therapeutic agent as described above. Thus, it will be understood that the first build material, the second build material, and the third build material may be the same material (e.g., a single material or a blend of materials such as a blend of polymers) or different materials. When using the same materials, achieving different material characteristics for one or more of the different portions may be accomplished through adjustment of build parameters in the additive manufacturing process such as extrusion rate, extrusion height, temperature, and so on.

It will be understood that other manufacturing techniques besides electrospinning and three-dimensional printing may also or instead be used to create a fluid conduit as described herein such as other additive manufacturing techniques, casting, melt spinning, pore forming using a solvent or the like, gamma ray manufacturing, and the like. By way of example, a spin bath may be utilized in manufacturing a fluid conduit as described herein. Also or instead, forming a fluid conduit according to the present teachings may include extruding material with a pore-forming agent, e.g., intermittently extruding the pore-forming agent during a spinning process (e.g., melt spinning or electrospinning). Moreover, when using an extrusion based technique, a plurality of extrusion nozzles may be used simultaneously or alternatively—e.g., for intermittent changes between forming porous and non-porous portions of a fluid conduit as described herein.

Although many embodiments described herein include an example of a fluid conduit having ends that are substantially non-porous with a substantially porous portion formed in-between, the present teachings shall be understood to include fluid conduits having other portions—for example, more than one substantially porous portions and/or more than two substantially non-porous portions. Also, or instead, the present teachings may include a device utilizing a plurality of fluid conduits as described herein—e.g., as used in bundles in a dialyzer.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random-access memory associated with a processor), or a storage device such as a disk drive, flash memory or any other optical, electromagnetic, magnetic, infrared, or other device or combination of devices. In another aspect, any of the systems and methods described above may be embodied in any suitable transmission or propagation medium carrying computer-executable code and/or any inputs or outputs from same.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings.

Unless the context clearly requires otherwise, throughout the description, the words "comprise," "comprising," "include," "including," and the like are to be construed in an inclusive sense as opposed to an exclusive or exhaustive sense; that is to say, in a sense of "including, but not limited to." Additionally, the words "herein," "hereunder," "above," "below," and words of similar import refer to this application as a whole and not to any particular portions of this application.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A system, comprising:
   a drain structurally configured for connection to a bladder of a patient;
   a fluid conduit structurally configured for connection with a vascular system of the patient and for fluid communication with the drain, the fluid conduit comprising:
      a first portion having a first porosity;
      a second portion disposed immediately adjacent to the first portion, the second portion having a second porosity that is greater than the first porosity, wherein the second porosity is configured to permit a predetermined filtrate transport through the second portion and into the drain; and
      a third portion disposed immediately adjacent to the second portion, the third portion having a third porosity that is less than the second porosity, wherein each of the first portion, the second portion, and the third portion are integrally formed as a single, continuous piece defining the fluid conduit; and
   a pump configured to control a flow of filtrate from the fluid conduit through the drain.

2. The system of claim 1, further comprising a housing, wherein the fluid conduit is at least partially contained within the housing.

3. The system of claim 2, wherein the drain is in fluid communication with the housing such that the predetermined filtrate transport through the second portion is configured to flow into the housing and into the drain.

4. The system of claim 1, wherein the pump is structurally configured for implantation within the patient.

5. The system of claim 4, wherein the pump is powered by a battery.

6. The system of claim 5, wherein the battery is configured for charging through skin of the patient.

7. The system of claim 1, wherein the pump is further configured for removal of fluid from an abdominal cavity of the patient.

8. The system of claim 1, wherein the pump is controllable to adjust one or more of a pressure gradient and an ultrafiltration flow rate in the system.

9. The system of claim 1, wherein the system is configured to provide an ultrafiltration volume of at least 1.5 liters per 24 hours.

10. The system of claim 1, wherein the system is configured to provide an ultrafiltration volume of up to and including 3 liters per 24 hours.

11. The system of claim 1, wherein the system is configured to provide a mean ultrafiltration rate of at least 1 milliliter per minute.

12. The system of claim 1, wherein the system is configured to provide a mean ultrafiltration rate of up to and including 2.1 milliliters per minute.

13. The system of claim 1, further comprising a valve configured to further control the flow of filtrate from the fluid conduit through the drain.

14. The system of claim 1, wherein each of the first portion and the third portion of the fluid conduit is sized and shaped for anastomosis with a blood vessel of the patient.

15. The system of claim 1, wherein the second porosity has a molecular weight cutoff below 70 kilodaltons (kDa).

16. The system of claim 1, wherein an internal diameter of the fluid conduit is about 6 millimeters.

17. The system of claim 1, wherein the fluid conduit is formed during an electrospinning process.

18. The system of claim 1, wherein a material used to form the fluid conduit includes a therapeutic agent.

19. The system of claim 1, wherein the fluid conduit lacks interfaces between the first portion, the second portion, and the third portion.

20. The system of claim 1, wherein the drain includes a catheter for connecting to the bladder of the patient.

* * * * *